United States Patent [19]
Bucalo

[11] 3,931,820
[45] Jan. 13, 1976

[54] LUMEN REAMER

[75] Inventor: Louis Bucalo, Holbrook, N.Y.

[73] Assignee: Investors in Ventures, Inc., New York, N.Y.

[22] Filed: Apr. 18, 1974

[21] Appl. No.: 461,981

Related U.S. Application Data

[63] Continuation-in-part of Ser. No. 359,429, May 11, 1973, Pat. No. 3,815,578.

[52] U.S. Cl............ 128/304; 15/104.1 R; 30/279 R; 128/2 B; 408/226
[51] Int. Cl.² ................................. A61B 17/22
[58] Field of Search............ 128/2 B, 304, 305, 311; 30/279 R; 15/104.1 R; 408/226, 227

[56] References Cited
UNITED STATES PATENTS

| | | | |
|---|---|---|---|
| 2,437,329 | 3/1948 | Moore | 128/304 |
| 2,730,101 | 1/1956 | Hoffman | 128/305 |
| 2,787,010 | 4/1957 | Uphoff | 408/226 X |

FOREIGN PATENTS OR APPLICATIONS

| | | | |
|---|---|---|---|
| 166,449 | 11/1964 | U.S.S.R. | 128/305 |

Primary Examiner—Dalton L. Truluck
Attorney, Agent, or Firm—Steinberg & Blake

[57] ABSTRACT

A reamer, particularly for removing mucosa from the lumen of a tubular body organ. The reamer has an elongated reaming portion to one end of which a handle is fixed. The reaming portion is hollow and of polygonal cross section so that it is made up of a plurality of walls distributed about an axis of the reaming portion. At locations where these walls would normally intersect, the reaming portion is formed with slots, the edges of which form reaming edges.

7 Claims, 10 Drawing Figures

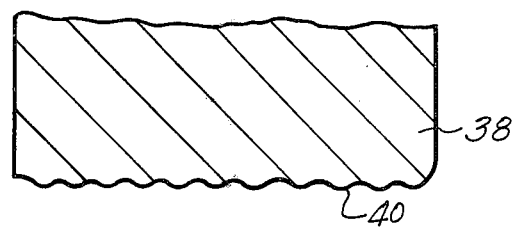
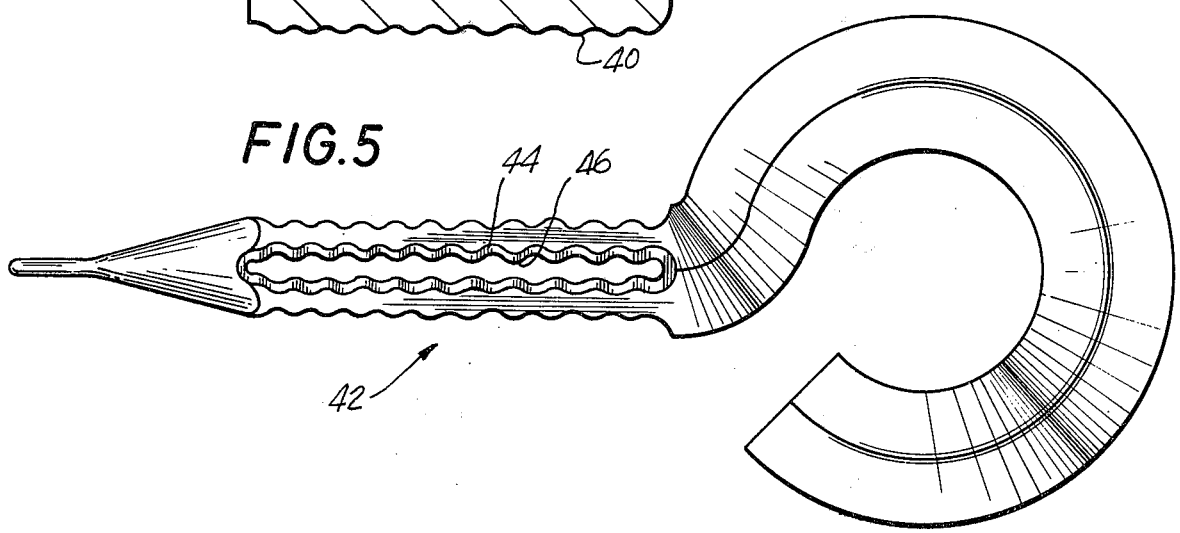
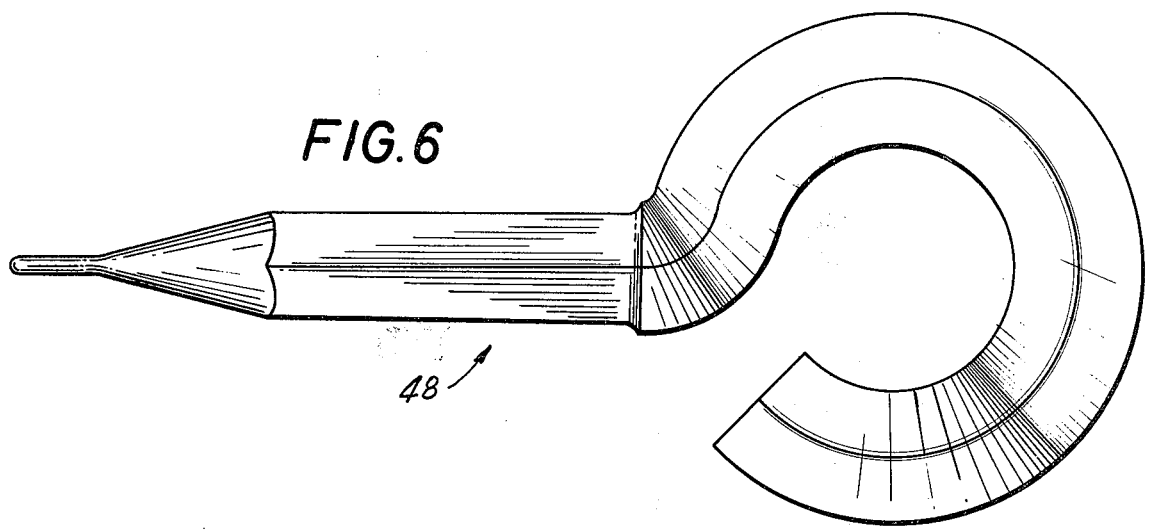
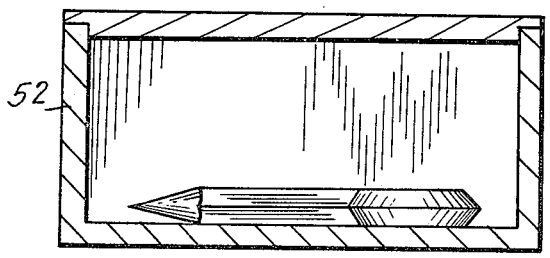
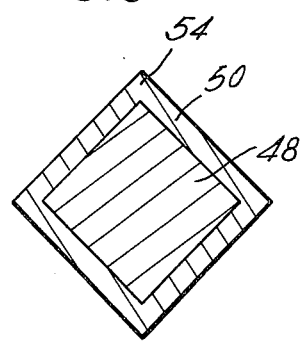
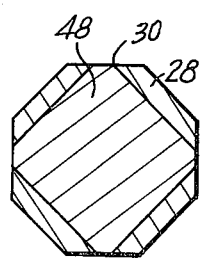

LUMEN REAMER

CROSS REFERENCE TO RELATED APPLICATION

This application is a continuation-in-part of copending application Ser. No. 359,429, filed May 11, 1973, now U.S. Pat. No. 3,815,578, issued June 11, 1974, and entitled "Method of Inserting An Implant Into a Portion of a Tubular Organ Whose Mucous Lining has Been Partially Removed".

BACKGROUND OF THE INVENTION

The present invention relates to reamers.

In particular, the present invention relates to reamers designed for the special purpose of removing mucosa from the lumen of a tubular body organ.

As is well known, when an implant is introduced into a tubular body organ, it is desirable to cause the tissue of the tubular body organ to grow into the pores of an ingrowth means carried by the implant at the exterior thereof. The growth of tissue into the ingrowth means is enhanced by removing mucosa at least from that part of the inner surface of the tubular body organ which engages the ingrowth means.

A reamer of this type must meet certain requirements. Thus, a simple elongated body having a roughened surface will indeed suffice to remove mucosa, but the roughened surface rapidly becomes plugged with the mucosa and an efficient removal of the mucosa cannot be achieved with such a reamer. In other words, provision must be made for receiving the removed mucosa in such a way that it will not interfere with the operation of the reamer, while at the same time assuring a reaming action which will cleanly and quickly remove the mucosa without undesirably damaging the body tissue from which the mucosa is removed.

SUMMARY OF THE INVENTION

It is accordingly a primary object of the present invention to provide a reamer which will fulfill these requirements.

Thus, it is an object of the present invention to provide a reamer capable of quickly and effectively removing mucosa from a desired area while at the same time preventing inefficient reamer operation by the mucosa itself.

The reamer of the invention includes an elongated hollow reaming portion of polygonal cross section having a plurality of walls distributed about an axis of the reaming portion, this reaming portion being formed with slots at locations where the walls otherwise would intersect. The edges of these slots perform the reaming action with the removed mucosa entering through the slots into the hollow interior of the reamer. A handle means is fixed to the reaming portion at one end region thereof.

BRIEF DESCRIPTION OF DRAWINGS

The invention is illustrated by way of example in the accompanying drawings which form part of this application and in which:

FIG. 4 is a fragmentary schematic sectional elevation of a grinding wheel which may be used in the manufacture of a reamer of the invention;

FIG. 5 is a side elevation of another embodiment of a reamer according to the invention;

FIG. 6 shows in elevation a mandrel which may be used in the method of manufacture of the reamer of FIG. 1 or the reamer of FIG. 5;

FIG. 7 schematically illustrates how a coating is deposited on the mandrel of FIG. 6;

FIG. 8 shows in cross section part of the mandrel with the coating thereon;

FIG. 9 shows the structure of FIG. 8 after the corners have been removed; and

DESCRIPTION OF PREFERRED EMBODIMENTS

Figure 1:
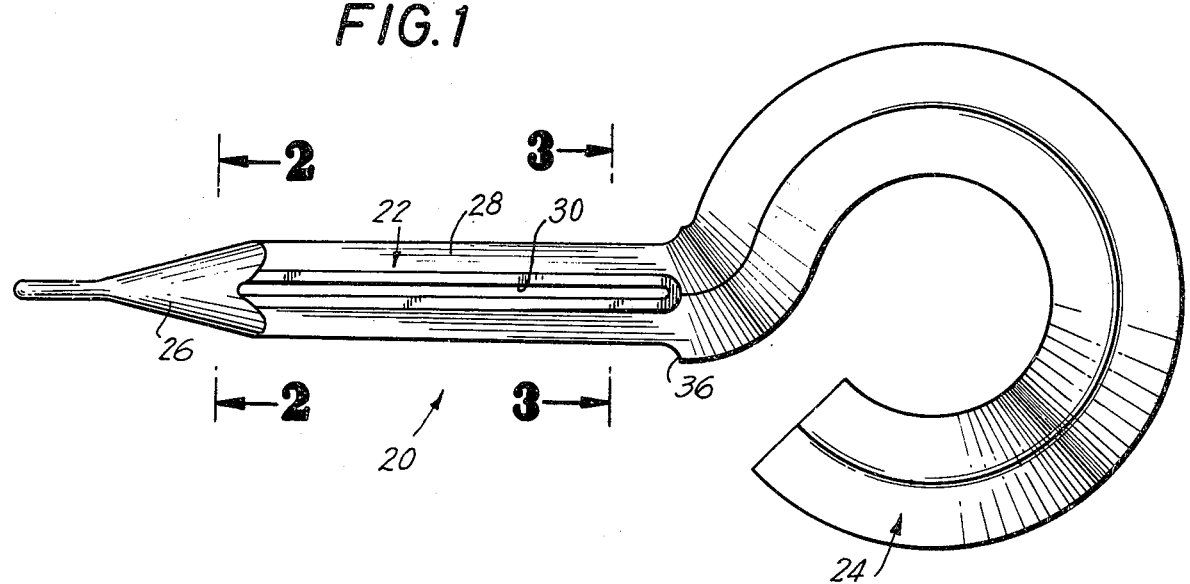
FIG. 1 is a side elevation of one embodiment of a reamer according to the invention.
Figure 2:
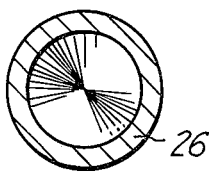
FIG. 2 and 3 are respectively transverse sections of the structure of FIG. 1 taken respectively along lines 2—2 and 3—3 of FIG. 1 in the direction of the arrows.
Figure 3:
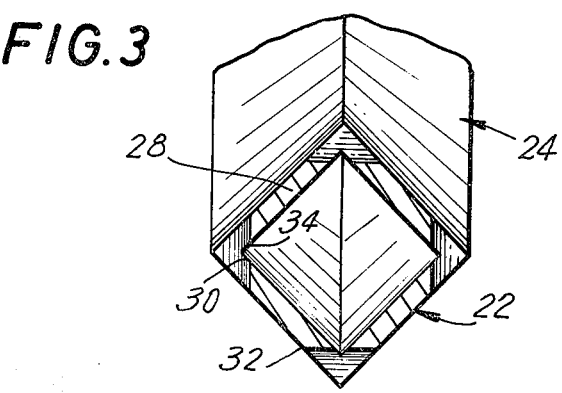

Referring first to FIGS. 1–3, the reamer 20 which is illustrated therein has an elongated reaming portion 22 to an end of which a handle means 24 is fixed, this handle means being curved in the illustrated example. The entire reamer 20 in the example of FIG. 1 is made of a suitable metal such as nickel. The elongated reaming portion 22 as well as the handle means 24 are hollow and integrally formed of a one-piece body. The hollow elongated metal body is of a polygonal cross section. In the illustrated example this cross section is of a square configuration, as is apparent from FIG. 3. However, at its left end region, as viewed in FIG. 1, the reaming portion 22 tapers so as to have a pointed end region 26 facilitating introduction of the reamer into a tubular body organ. This hollow pointed portion 26 is of a circular cross section, as is apparent from FIG. 2.

As may be seen from FIG. 3, the elongated central axis of the reamer portion 22 is surrounded by a plurality of walls 28, and slots 30 are formed at the locations along the reaming portion 22 where the walls 28 otherwise would intersect.

The edges which form the slots 30 form at the outer surfaces of the walls 28 reaming or cutting edges 32 while the inner edges 34 define the elongated openings or slots through which removed mucosa can enter into the hollow interior of the reaming portion 22. Thus in the illustrated example where the reamer is of a square cross section there are eight cutting edges 32 several of which will become operative during rotary movement of the reamer, and the removed mucosa will readily enter through the spaces between the edges 34 of the slots 30 into the hollow interior of the reamer. After use the removed mucosa can readily be washed out through the slots.

In order to use the reamer, after an incision is made to give axis to the lumen of the tubular body organ, the reamer is introduced with the pointed end 26 facilitating introduction of the reamer. The reamer may be introduced until the shoulder 36 (FIG. 1) engages an end of the tubular organ where the incision has been formed, and the length of the slots 30 is such that upon removal of mucosa that part of the surface of the tubular organ in the interior thereof which will engage an ingrowth means will have the mucosa removed therefrom. After the mucosa is quickly and easily removed with this reamer 20 of the invention, the reamer is removed and the implant is introduced.

In the illustrated example the slots 30 are formed by grinding away corners of the hollow reamer portion 22 with a grinding wheel having a grinding surface forming part of a simple right cylinder, thus providing the straight slots 30. However, it is also possible to use for this purpose, as shown in FIG. 4, a grinding wheel 38 having a wavy grinding surface 40. In this way a reamer 42 is provided as illustrated in FIG. 5. This reamer 42 is identical with the reamer 20 except that the edges 44 of the several slots 46 have the illustrated wavy configuration, thus achieving a "steak knife" effect. These wavy reaming edges 44 which define the slots 46 provide an even more effective reaming action. Thus these wavy edges serve to remove mucosa as a result of axial as well as rotary movement of the reamer.

FIGS. 6–9 illustrate the method of manufacturing the reamer. Thus, as may be seen from FIG. 6 initially a mandrel 48 is provided. This mandrel is solid and has a configuration conforming to that of the finished reamer. The mandrel 48 may be made of a material such as aluminum. This mandrel has a coating 50 deposited thereon. This coating 50 is shown in cross section on the mandrel 48 in FIG. 8. As is indicated in FIG. 7, the coating may be deposited in a number of different ways. Thus the coating may be provided by vapor deposition in a suitable evacuated atmosphere, provided in the interior of a suitable enclosure 52 as schematically illustrated in FIG. 7. However, it is equally possible to provide the nickel coating on the aluminum mandrel by electrolytic deposition. Other types of metal deposition may be used. It is only required that the deposited coating build up to a desired thickness on the mandrel and that the material used for the coating have a melting point which is substantially higher than the melting point of the mandrel. These requirements are met by depositing nickel on aluminum, but of course it is also possible to deposit other coating materials on mandrels made of other materials which are of a lower melting point. For example, may metals can be deposited on a plastic mandrel which will have a melting point lower than that of the deposited metal. In order to provide for electrolytic deposition with such materials, the plastic mandrel can be coated with graphite, for example, so that its exterior surface is rendered electrically conductive to enable the electrolytic deposition to take place.

With the coating 50 thus deposited on the mandrel 48, as shown in FIG. 8, corners of the deposited coating are removed to provide the structure shown in section in FIG. 9. Thus, it will be seen from FIG. 9 that the separate walls 28 are still situated around the mandrel 48, but the corners 54 have been removed along the reaming portion behind the pointed end thereof through a sufficient length along the reaming portion and to an extent sufficient to form the slots 30.

At this time the mandrel 40 with the coating thereon is exposed to a temperature sufficiently high to melt the mandrel but insufficiently high to soften the deposited coating. For this purpose the structure may be located in a suitable oven with a suitable dish or other receptacle situated beneath the coated mandrel, which is supported on a suitable hanger, so as to catch the molten mandrel material which upon melting will flow out through one or more of the slots 30, the structure being supported in such a way that one of the slots 30 is situated at an elevation low enough to permit the entire mandrel to flow out through at least this one slot. Upon removal of the structure from an oven or the like in which the melting of the mandrel has taken place, the remaining coating which forms the reamer can be tilted to enable any residual molten mandrel material to flow out through one or more of the slots.

In this simple way it is possible to provide either the mandrel of FIG. 1 or the mandrel of FIG. 5.

Figure 10:
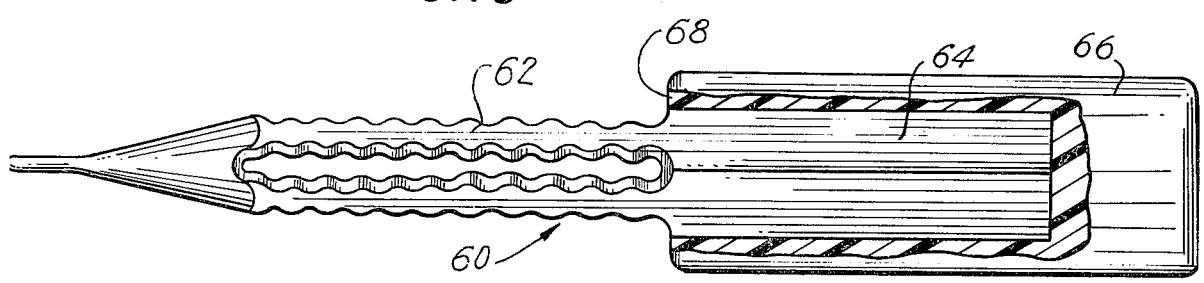
FIG. 10 is a partly sectional illustration of another embodiment of a reamer according to the invention.

However, it is not essential to have a curved handle means 24. As may be seen from FIG. 10, the reamer 60 has an elongated straight reaming portion 62 which may be identical with the straight reaming portion of the reamer 42 of FIG. 5. However, in this case the mandrel is straight and is coated so as to provide an elongated hollow extension 64 of square cross section extending beyond the reaming portion 62. A simple plastic handle 66 is provided with a bore of square cross section to receive the extension 64 as shown in FIG. 10. This extension 64 is situated in the plastic handle 66 with a suitably tight friction fit, for example, so that in this simple way the reamer 10 can readily be manufactured. With this construction of FIG. 10 the inner end surface 68 of the handle 66 serves as a guide for determining the distance through which the reamer is introduced into the tubular body organ, so that this surface 68 performs a function similar to the shoulder 36 of FIG. 1.

It is to be emphasized that the structure is shown in the drawings at a scale which is far greater than its actual size. The reamer of the invention may be introduced into the interior of a tubular organ such as a vas deferens, and the cross section of the reamer is extremely small so that it can conveniently be received in the interior of such a tubular organ for effectively removing the mucosa therefrom. In spite of these extremely small dimensions, as a result of the method of manufacture it becomes possible to produce the reamer of the invention both inexpensively as well as with a precise construction which will achieve the desired results in a highly effective manner.

What is claimed is:

1. A reamer, particularly for removing mucosa from the lumen of a tubular body organ, comprising an elongated hollow, substantially rigid reaming portion and handle means fixed to and extending from said reaming portion at a rear end region thereof, said reaming portion having a free front end region distant from said rear end region thereof, having a central axis, being of a polygonal cross section, and including a plurality of substantially rigid, flat walls distributed about and extending parallel to said axis, said walls being stationary with respect to each other and being integral with said front free end portion, said reaming portion being formed with a plurality of slots extending parallel to said axis rearwardly of said front free end portion at locations where said walls would intersect if said slots were not present, and said walls having at said slots reaming edges which remove a material such as mucosa with the material entering through the slots into the interior of the reaming portion.

2. The combination of claim 1 and wherein said reaming portion is made of metal.

3. The combination of claim 2 and wherein said slots have straight edges.

4. The combination of claim 2 and wherein said slots have wavy edges.

5. The combination of claim 1 and wherein said reaming portion has a pointed configuration at its front end region distant from said handle means.

6. The combination of claim 1 and wherein said handle means forms an extension of said reaming portion.

7. The combination of claim 1 and wherein said handle means includes a body formed with a bore, said reaming portion carrying at the end region where said handle means is located an elongated extension received in said bore for fixing said body to said reaming portion.

* * * * *